United States Patent
Wöhrle et al.

(10) Patent No.: US 6,329,562 B1
(45) Date of Patent: Dec. 11, 2001

(54) SEPARATION PROCESS FOR SEPARATING CYCLOALKENES HAVING AT LEAST 2 DOUBLE BONDS FROM A REACTION MIXTURE

(75) Inventors: Ingo Wöhrle, Holzminden; Peter-Reinhard Schick, Leverkusen, both of (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 09/605,909

(22) Filed: Jun. 28, 2000

(30) Foreign Application Priority Data

Jul. 8, 1999 (DE) ................................. 199 31 711

(51) Int. Cl.$^7$ ............................ C10G 25/00; C07C 7/12
(52) U.S. Cl. ...................... 585/820; 585/827; 585/831; 208/310 Z
(58) Field of Search ................... 585/820, 827, 585/831; 208/310 Z

(56) References Cited

U.S. PATENT DOCUMENTS

| | | | | |
|---|---|---|---|---|
| 3,376,354 | * | 4/1968 | Kroll et al. ......................... | 585/827 |
| 3,832,416 | * | 8/1974 | Van Grinsven ..................... | 585/827 |
| 3,935,270 | | 1/1976 | Calderon ........................... | 260/586 P |
| 4,313,014 | | 1/1982 | Kondo et al. ....................... | 585/827 |
| 4,336,410 | * | 6/1982 | Kondo ............................... | 585/827 |
| 4,668,836 | | 5/1987 | Eberle et al. ....................... | 585/364 |

FOREIGN PATENT DOCUMENTS

| | | |
|---|---|---|
| 1325642 | 12/1993 | (CA) . |
| 1105565 | 3/1968 | (GB) . |
| 1118517 | 7/1968 | (GB) . |

OTHER PUBLICATIONS

Chemical Abstracts, vol. 87, No. 5, Aug. 1, 1977, Columbus, Ohio, US; abstract No. 39009f, Seite 477; XP002146078, Zusammenfassung, & JP 51 146436 A (Kanegafuchi Chemical Industry Co) Dec. 16, 1976.
S. Warwel et al, Seife–Ole–Fette–Wachse 115, (month unavailable) 1989 pp. 538–545, Synthesen von Moschus–Riechstoffen durch Olefin–Metathese.
Warwel et al, Chemiker–Zrg. 107, pp. 115–120, (month unavailable) 1983, Olefinsynthesen Durch Methathese.

* cited by examiner

Primary Examiner—Walter D. Griffin
Assistant Examiner—Tam M. Nguyen
(74) Attorney, Agent, or Firm—Joseph C. Gil; Noland J. Cheung

(57) ABSTRACT

A process for separating off cycloalkenes having at least two double bonds from a reaction mixture in hydrocarbon solution formed during the metathesis of cycloalkamonoenes or cyclomonoene/cyclopolyene mixtures comprising the steps of treating the reaction mixture with zeolites in the liquid phase, absorbing the olefins having at least two double bonds present in the solution by the zeolite, separating off the laden zeolite, and obtaining the cycloalkadienes and cyclopolyenes by desorption.

6 Claims, No Drawings

SEPARATION PROCESS FOR SEPARATING CYCLOALKENES HAVING AT LEAST 2 DOUBLE BONDS FROM A REACTION MIXTURE

FIELD OF THE INVENTION

The invention relates to a process for separating off cycloal-kadienes and cyclopolyenes from the reaction mixture formed during the metathesis of cycloalkenes using zeolites, wherein the cyclopolyenes have at least two double bonds.

BACKGROUND OF THE INVENTION

Macrocyclic alkenes having 8 to 20 carbon atoms can be used as intermediates for the preparation of fragrances. 14- to 17-membered cycloalkadienes are used in particular as starting materials for the preparation of musk fragrances. Cyclohexadecenone can be prepared from cyclohexadeca-1,9-diene (S. Warwel, H. Bachem, N. Döring, H. Kätker, E. Rose in Seife-Öle-Fette-Wachse 115, 538 (1989)). In general, it is necessary for the starting compounds to be virtually free from impurities.

Cycloalkadienes are usually obtained by metathesis of corres-ponding cyclomonoenes. By way of example, metatheses, which may be mentioned are those described in U.S. Pat. No. 3,935,270, Brit. Pat. No. 1,105,565, Brit. Pat. No. 1,118,517, EP 182 333, and also Warwel, H. Ridder, G. Hachen in Chemiker-Ztg. 107, 115 (1983).

A disadvantage of these processes is the large amount of solvent, which has to be used to ensure high selectivity for desired cycloal-kadienes. The known isolation processes are saddled with high-energy costs and are therefore expensive. Isolation is usually carried out by means of distillation.

The metathesis of cyclooctene or cyclopolyoctenylenes to give cyclohexadecadiene is carried out as described, for example, in EP 182 333 and EP 343 437. In the liquid phase, the mixture of starting materials is brought into contact with the heterogeneous catalyst system $Re_2O_7$/gamma-$Al_2O_3$ in the presence of a tetraalkyltin.

The reaction is preferably carried out at temperatures of from 20 to 60° C. and using from 0.01 to 0.05 molar solutions. The contact time on the catalyst is typically from 25 to 200 seconds. The molar concentration of the solutions, which is given, refers to the calculated cyclomonoene units, which result from the division of the cyclopolyenes into monomers.

In the process described above, cyclooctene or a cyclooctene/cyclopolyoctenylene mixture produces a reaction mixture, which essentially comprises cyclohexadecadiene, cyclotetracosatriene, cyclodotriacontatetraene, cyclotetracontapentaene and cyclooctatetracontahexaene. The proportion of cyclohexadecadiene is generally in the range from 20 to 50%, preferably from 25 to 35%.

In the same process, cyclooctene and cycloheptene produce a reaction mixture, which comprises cyclotetradeca-1,8-diene, cyclopenta-1,8-diene and cyclohexadeca-1,9-diene, and higher macrocyclic cyclopolyenes. The proportion of dienes is generally in the range from 20 to 50% preferably from 25 to 40%.

The reaction mixture is usually in the form of a solution in metathesis inert solvents.

In the above-process, the preferred solvents here are unbranched or cyclic hydrocarbons. The unbranched are compounds having from 5 to 12 carbon atoms, preferably from 5 to 8 carbon atoms, for example n-pentane and n-hexane. The cyclic hydrocarbons are compounds having from 5 to 8 carbon atoms, preferably from 5 to 6 carbon atoms, for example cyclohexane.

It is known that crystalline aluminum silicates (zeolites) can be used for separating hydrocarbons. Thus, for example, U.S. Pat. No. 3,668,730 describes large-pored zeolites for separating xylenes. In U.S. Pat. No. 4,313,014, such zeolites are used for separating off cyclohexenes.

SUMMARY OF THE INVENTION

We have now found a process for separating off cycloalkenes having at least two double bonds from a reaction mixture in hydrocarbon solution formed during the metathesis of cycloalkamonoenes or cyclomonoene/cyclopolyene mixtures. The process is characterized in that the reaction mixture is treated with zeolites in the liquid phase, the olefins having at least two double bonds present in the solution are adsorbed by the zeolite, the laden zeolite is separated off, and cycloalkadienes and cyclopolyenes are obtained by desorption.

DETAILED DESCRIPTION OF THE INVENTION

Surprisingly, it has been found that adsorbents of the faujasite type, such as, for example, the zeolites of type X and Y in the alkali metal and alkaline earth metal form, are very suitable adsorbents for macrocyclic compounds which have a critical diameter which is much larger than the pore opening of these zeolites.

The cycloalkadienes or cyclopolyenes contain at least 8 carbon atoms in the ring, preference being given to ring sizes with more than 11 carbon atoms.

Furthermore, it has been found that said zeolites affect selective adsorption of the cycloalkadienes. From the above-described product mixtures of the metathesis of cyclooctene and cyclopolyoctenylenes, it is possible to achieve a stepwise depletion of the dienes from the crude solution. Here, depletion in the solution takes place in the order cis,cis-cyclohexadeca-1,9-diene, followed by cis,trans-cyclohexadeca-1,9-diene. The trans,trans-cyclohexadeca-1,9-diene remains in the solution the longest and becomes concentrated therein. cis,cis-Cyclohexadeca-1,9-diene can be separated off from very dilute solutions using aluminum silicates of the X an d Y type e in the sodium or a ammonium form. The adsorption is particularly gentle and efficient on exposure to ultrasound waves.

Amorphous adsorbents, such as, for example, silica gels of varying grain size and porosity, basic, acidic or neutral aluminum oxides and also noncrystalline aluminum silicates of varying compositions did not effect the desired adsorption.

Type X aluminum silicates are zeolites which have a faujasite crystalline structure. These well-known zeolites can be described using the following formula:

$M_{2/n}OAl_2O_3xSiO_2yH_2O$ n: valency of the metal M
x: a number between 2 and 3
y: water of crystallization
Any type X aluminum silicate can be used, and these materials are commercially available.

Type Y aluminum silicates are zeolites which have a faujasite crystalline structure. These well known zeolites can be described using the following formula:

$$M_{2/n}O Al_2O_3 x SiO_2 y H_2O$$

n: valency of the metal M
x: a number between 3 and 6
y: water of crystallization Any type Y aluminum silicate can be used, and these materials are commercially available.

Prior to carrying out the adsorption, the water of crystallization must be removed from the zeolites. At temperatures between 150 and 650° C., optionally under reduced pressure, the majority of the water is removed from the zeolite. If this activation is carried out at lower temperatures, only partial dehydration takes place and the loading capacity of the adsorbent is reduced.

Zeolites for the process according to the present invention are large-pored zeolites of type X or Y, which can comprise any type of metal cation. Some of the cations can also be replaced for protons or ammonium ions. The pure H form of the Y zeolite has high catalytic activity which, at elevated temperature, can lead to isomerization of double bonds and carbon backbone. It is likewise possible for two or more different metal ions to be replaced. Preference is given to cations of main groups I and II of the Periodic Table of the Elements. Particular preference is given to the sodium and calcium forms.

The zeolites can be in the form of powders, spheres, rods, cylinders, extruded bars or in other moldings.

The adsorption of the cycloalkadienes and cyclopolyenes from the reaction mixture onto the zeolite takes place at temperatures in the range from 0 to 150° C., preferably in the range from 40 to 100° C.

Adsorption according to the process of the present invention generally requires from 15 minutes to 8 hours, preferably from 1 to 4 hours.

According to the present invention, from 5 to 50 parts by weight, preferably from 10 to 25 parts by weight, of zeolite are used, based on 1 part by weight of cycloalkenes.

The desorption generally takes place using a compound which is chemically and thermally stable under desorption conditions. It must be possible to separate off and recover this low-cost chemical from the extract in sufficient purity in a simple manner.

According to the present invention, the desorption is carried out using aromatic hydrocarbons. Other compounds, such as ethyl acetate or isopropanol, can likewise be used, although, in these cases, the desorption takes place more slowly. Polar desorbents, i.e. solvents used for the desorption, such as, for example, ammonia water, diols and also amino alcohols were unsuccessful.

Aromatic hydrocarbons which may be mentioned are compounds having from 6 to 12 carbon atoms, preferably from 6 to 9 carbon atoms such as, for example, benzene, toluene, ethylbenzene, xylene and trimethylbenzene.

During the desorption, the temperature should not be significantly greater than 150° C., since otherwise isomerization products can be found. The zeolite can then turn from white to beige.

In the process according to the present invention, the zeolite did not change color and the olefins did not undergo isomerization reactions.

Adsorption and desorption can be carried out at from 0 to 30 bar, preference being given to pressures in the range from 1 to 10 bar.

In the process according to the present invention, largely complete desorption generally requires from 15 minutes to 20 hours, preferably from 2 to 10 hours, depending on the zeolite molding.

After the adsorber material has been regenerated it can be reused without significant loss in adsorption capacity. For regeneration, the majority of the desorbent still adhering to the adsorbent is removed under reduced pressure. After a time, it is advisable to burn clean the zeolite, since after a few cycles it is possible, depending on the composition of the solution of the olefins investigated, for the surface to become partially coated with higher oligomers or polymers.

The desorbent is removed from the adsorbent at pressures between 0 and 1 bar, preferably at pressures below 100 mbar. The temperature is in the range from 30 to 300° C., preferably in the range from 100 to 220° C.

The adsorbent was generally burnt off at temperatures of from 300 to 700° C., preferably in the range from 400 to 550° C. in a stream of air.

The process according to the present invention can, for example, be carried out as follows:

A highly diluted solution of cycloalkenes is brought into contact in the liquid phase in an inert solvent with a dried/dehydrated, i.e. activated, zeolite of the X or Y type for several hours. The aluminum silicate adsorbs those substrates, which contain at least two double bonds and at least 8 carbon atoms. When adsorption is complete, the laden zeolite is filtered off, washed and dried. The adsorbed substrates are then desorbed, for example, by displacement with aromatic hydrocarbons. The olefinic substrates are freed from the desorbent, and the desired olefins are isolated.

The invention is further illustrated but is not intended to be limited by the following examples in which all parts and percentages are by weight unless otherwise specified.

EXAMPLES

Example 1

As adsorbent, commercially available zeolite NaX (Siliporite 10A, a product from Elf Atochem/CECA) in powder form was calcined in the air for 12 hours at 450° C.

12 g of the activated zeolite NaX and a solution of 1 g of all-trans 1,5,9-cyclododecatriene (>99% purity, obtained from Aldrich) in 200 ml of n-hexane at 65° C. After 1 to 2 hours, the solution was cooled to room temperature and the zeolite was separated off. The solution which remained comprised <1% of the original amount of triene.

For the desorption, the zeolite was transferred to an extraction thimble and treated with 50 ml of boiling toluene for 3 hours in a Soxhlet apparatus.

When desorption was complete, the extract was freed from toluene by distillation. 0.96 g of a liquid residue were obtained, which comprised all-trans 1,5,9-cyclododecatriene with a GC purity of >98%.

Example 2

As adsorbent, commercially available zeolite NaX (Siliporite 10A, a product from Elf Atochem/CECA) in powder form was calcined in the air for 12 hours at 450° C.

The adsorption of the metathesis crude solution formed by the above-described metathesis of a 0.024 molar solution in n-hexane of a cyclooctene/cycloheptene mixture in the molar ratio 1:1 was analyzed (2.49 g of olefins/l).

50 g of the activated zeolite NaX were stirred with 1200 ml of a metathesis crude solution at 65° C. for 2 hours.

After this time, almost all of the compounds having two or more double bonds had been adsorbed (>98%, GC check).

The laden zeolite was separated off and washed with a little n-hexane. The still adherent n-hexane was then largely removed at 50° C./1 mbar.

For the desorption, the zeolite was transferred to an extraction thimble and treated with 100 ml of boiling toluene in a Soxhlet apparatus for 5 hours.

When desorption was complete, the extract was freed from toluene by distillation. 2.72 g of a liquid residue were obtained which have a product distribution which is largely identical to the starting mixture.

Example 3

As adsorbent, commercially available zeolite CaX (a product from Grace Davison) in powder form was calcined in the air at 450° C. for 12 hours.

The adsorption of the reaction solution formed by the above-described metathesis of cyclooctene (2.4 g/l in n-hexane) was analyzed. The reaction solution typically comprised 5% cyclooctene, 30% cyclohexadeca-1,9-diene, 33% trienes, 18% tetraenes, 9% pentaenes and 4% hexaenes.

60 g of the activated zeolite CaX were stirred with 1400 ml of a metathesis crude solution at 65° C. for 1 to 3 hours.

After this time, almost all of the compounds having two or more double bonds had been adsorbed (>98%, GC check).

Further isolation was carried out as described in Example 2.

3.05 g of a liquid residue were obtained which had a product distribution which was largely identical to the starting mixture.

Example 4

As adsorbent, commercially available zeolite NaX (Siliporite 10A, a product from Elf Atochem/CECA) in spherical form was calcined in the air at 450° C. for 12 hours.

The adsorption of the reaction solution formed by the above-described metathesis of cyclooctene (2.8 g/l in n-hexane) was analyzed. The reaction solution exhibited the product distribution listed in Example 3.

100 g of the activated zeolite in spherical form were introduced into a vertically constructed heatable tubular reactor. The zeolite bed is heated to 65° C. 2000 ml of the metathesis crude solution were circulated using a hose pump, the adsorbate flowing through the zeolite bed from bottom to top. The amount conveyed was from 2000 to 5500 ml/h.

After 3 to 5 hours, almost all of the compounds having two or more double bonds had been adsorbed (>95%, GC check).

When adsorption was complete, the liquid was drained from the tubular reactor, and the laden zeolite was washed with a little n-hexane. Most of the still adherent n-hexane was then removed at 50° C./1 mbar.

For desorption, the tube was heated to 120° C. 400 ml of ethylbenzene were circulated using a hose pump for from 5 to 8 hours, the desorbent flowing through the zeolite bed from bottom to top. The amount conveyed was from 500 to 2000 ml/h.

When desorption was complete, the extract was freed from ethylbenzene by distillation. 5.06 g of a liquid residue were obtained which had a product distribution which was largely identical to the starting mixture.

Example 5

As adsorbent, commercially available zeolite NaY (obtained from Strem Chemicals) in powder form was calcined in the air at 450° C. for 12 hours.

The selective concentration of cis,cis-cyclohexadeca-1,9-diene from the reaction solution formed by the above-described metathesis of cyclooctene (2.4 g/l in n-hexane) was analyzed. The reaction solution typically comprised 39% cyclohexadeca-1,9-diene, 32% trienes, 17% tetraenes, 8% pentaenes and 3% hexaenes.

The representative distribution of the diene double bond isomers was cis,cis: trans, cis: trans,trans=25: 58: 16.

8 g of the activated zeolite NaY were stirred with 500 ml of a metathesis crude solution at 65° C. for from 30 to 60 minutes.

After this time, according to GC, >92% of the cis,cis-cyclohexadeca-1,9-diene had been adsorbed.

Following removal of the laden NaY material, the solution, which remained, was subjected to further adsorption.

As adsorbent for the second adsorption, commercially available zeolite NaX (Siliporite 10A, a product from Elf Atochem/CECA) in powder form was calcined in the air at 450° C. for 12 hours.

20 g of the activated zeolite NaX were stirred with the metathesis crude solution at 65° C. for 2 to 3 hours.

After this time, virtually all of the compounds having two or more double bonds had been adsorbed (>98%, GC check).

The laden zeolite NaX was separated off and washed with a little n-hexane. Most of the still adherent n-hexane was then removed at 50° C./1 mbar.

For the desorption, the zeolite was transferred to an extraction thimble and treated with 100 ml of boiling toluene in a Soxhlet apparatus for 4 hours.

When desorption was complete, the extract was freed from toluene by distillation. 1.0 g of a liquid residue were obtained. The content of cis,cis-cyclohexadeca-1,9-diene in the residue was less than 0.5%.

Example 6

As adsorbent, commercially available zeolite NaX (Siliporite 10A, a product from Elf Atochem/CECA) in powder form was calcined in the air at 450° C. for 12 hours.

The adsorption of the reaction solution formed by the above-described metathesis of cyclooctene (2.4 g/l in n-hexane) was analyzed. The reaction solution exhibited the product distribution listed in Example 5.

25 g of the activated zeolite NaX were brought into contact with 500 ml of the metathesis crude solution in an ultrasound bath at 25 to 30° C. for 2 to 3 hours. The zeolite was then filtered off and the filtrate was analyzed by gas chromatography.

The solution which remained comprised <0.5% of cis,cis-cyclohexadeca-1,9-diene, and >94% of this substance had been adsorbed.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for separating off cycloalkenes having at least two double bonds from a reaction mixture in hydrocarbon solution formed during the metathesis of cycloalkamonoenes or cyclomonoene/cyclopolyene mixtures comprising the steps of treating the reaction mixture with a faujasite zeolite type in the liquid phase, absorbing the cycloalkenes having at least two double bonds present in the solution by the zeolite, separating off the laden zeolite, and obtaining the cycloalkenes by desorption.

2. A process according to claim 1, wherein said faujasite zeolite is an X or Y zeolite.

3. A process according to claim 1, wherein the cycloalkenes are cycloalkadienes wherein the selective adsorption of the cycloalkadienes is achieved by stepwise depletion of the dienes in the crude solution.

4. A process according to claim 1, wherein the adsorption is carried out in a temperature range from 0° to 150° C.

5. A process according to claim 1, wherein the adsorption is carried out over the course of from 15 minutes to 8 hours.

6. A process according to claim 1, wherein from 5 to 50 parts by weight of zeolite, based on 1 part by weight of cycloalkenes, is used.

\* \* \* \* \*